United States Patent [19]

Mueller et al.

[11] Patent Number: 5,037,949

[45] Date of Patent: Aug. 6, 1991

[54] POLYMERS PREPARED FROM 4,4'-BIS[2-(AMINO (HALO) PHENOXYPHENYL) HEXAFLUOROISOPROPYL]DIPHENYL ETHER

[75] Inventors: Werner H. Mueller, E. Greenwich; Dinesh N. Khanna; Rohitkumar H. Vora, both of W. Warwick, all of R.I.; Ruediger J. Erckel, Warren, N.J.

[73] Assignee: Hoechst Celanese Corp., Somerville, N.J.

[21] Appl. No.: 489,448

[22] Filed: Mar. 6, 1990

Related U.S. Application Data

[62] Division of Ser. No. 124,704, Nov. 24, 1987, Pat. No. 4,925,915.

[51] Int. Cl.$^5$ .................. C08G 69/26; C08G 8/02; C08G 14/00

[52] U.S. Cl. .................. 528/353; 528/125; 528/126; 528/128; 528/172; 528/173; 528/185; 528/188; 528/229; 528/352; 252/183.11

[58] Field of Search .............. 578/353, 125, 126, 128, 578/173, 172, 352, 229, 185, 188; 252/183.11

[56] References Cited

U.S. PATENT DOCUMENTS

| | | | |
|---|---|---|---|
| 3,356,648 | 12/1967 | Rogers | 528/353 |
| 4,111,906 | 9/1978 | Jones et al. | 528/229 |
| 4,477,648 | 10/1984 | Jones et al. | 528/185 |
| 4,542,257 | 9/1985 | Fraser et al. | 528/353 |
| 4,923,960 | 5/1990 | Chen, Sr. et al. | 528/173 |
| 4,925,915 | 5/1990 | Mueller et al. | 528/173 |
| 4,925,916 | 5/1990 | Harris et al. | 528/173 |
| 4,931,540 | 6/1990 | Mueller et al. | 528/173 |

*Primary Examiner*—John Kight, III
*Assistant Examiner*—P. Hampton-Hightower
*Attorney, Agent, or Firm*—M. W. Ferrell

[57] ABSTRACT

This invention relates to new fluorine-containing polyimides, polyamide-acids/esters, polyamides, addition polyimides and imide oligomers which exhibit low melting points, better solubilities, low dielectric constants, superior thermal and thermal oxidative stability, and improved processing characteristics.

The products of this invention are characterized by the fact that they are derived from 4,4'-bis[2-(amino(halo)-phenoxyphenyl)hexafluoroisopropyl]diphenyl ether.

21 Claims, No Drawings

POLYMERS PREPARED FROM 4,4'-BIS[2-(AMINO (HALO) PHENOXYPHENYL) HEXAFLUOROISOPROPYL]DIPHENYL ETHER

This is a divisional of application Ser. No. 124,704, filed Nov. 24, 1987, now U.S. Pat. No. 4,925,915.

FIELD OF THE INVENTION

This invention relates to new fluorine-containing polyimides, polyamide-acids/esters, polyamides, addition polyimides and imide oligomers which exhibit low melting points, better solubilities, low dielectric constants, superior thermal and thermal oxidative stability, and improved processing characteristics.

BACKGROUND OF THE INVENTION

Polyimides are widely used in the aerospace industry and electronics industry, because of their toughness, low density, thermal stability, radiation resistance and mechanical strength. However, it is recognized that polyimides are difficult to process. The processing problems arise from the insolubility of polyimides in most of the more common solvents. Consequently, products were fabricated from polyamide-acid intermediates, which are more soluble but less stable, and then imidized to provide the desired end product. The disadvantage of this process is that the water liberated during the imidization of the polyamide-acid forms undesirable voids o surface irregularities in the final product which reduce its mechanical properties.

Another approach is to provide a fully imidized prepolymer having reactive end groups. In this way, the water formed during imidization is removed before the final cure of the prepolymer. The resulting polyimide product is typically a thermoset plastic. However, the imidized prepolymers are not as soluble as would be desired.

It has been suggested that polyimides having a single hexafluoroisopropylidene linking group in the diamine or dianhydride comonomers have improved solubility properties. Several patents disclose polyimides prepared from diamines of this type. For example, U.S. Pat. No. 3,356,648 to Rogers discloses polyimides prepared from 2,2-bis(4-aminophenyl) hexafluoropropane; U.S. Pat. No. 4,592,925 to DuPont et al. discloses polyimides prepare from 2,2-bis(3-aminophenyl) hexafluoropropane; U.S. Pat. No. 4,111,906 to Jones et al. discloses polyimides prepared from 2,2-bis[4-(4-aminophenoxy)phenyl] hexafluoropropane; and U.S. Pat. No. 4,477,648 to Jones et al. discloses polyimides prepared from 2,2-bis[(2-halo-4-aminophenoxy)phenyl] hexafluoropropane.

SUMMARY OF THE INVENTION

The present invention seeks to provide polyimides and polyamides having improved solubility and processing characteristics by incorporating into the polymeric chain a novel aromatic diamine compound having two hexafluoroisopropylidene linking groups. The diamine may be characterized by the general formula:

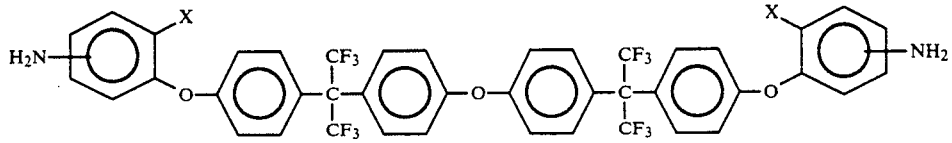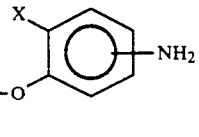

wherein X is hydrogen or halogen. The preferred diamine is 4,4'-bis[4-aminophenoxyphenyl)hexafluoroisopropyl] diphenyl ether. The polyimides are prepared by reacting these diamines with tetracarboxylic acids or derivatives thereof. The polyamides are prepared by reacting the diamines with the acid chlorides of dicarboxylic acids. It has been found that the polyimides of this invention also have low dielectric constants.

In another aspect, the invention also provides new monomers, oligomers and their corresponding addition polyimides. The monomers and oligomers are formed by reacting the new diamines with dianhydrides and reactive end-capping compounds such as aromatic ethynyl amines, nadic anhydrides, benzocyclobutenes, or maleic anhydrides. The resulting imide monomers and oligomers may then be cured by addition reactions.

In yet another aspect, the invention provides polymer precursor compositions, epoxy resin hardeners, matrix resins, composites, laminates, films, fibers, adhesives, coatings, photoresists and molded articles.

DETAILED DESCRIPTION OF THE INVENTION

The polyimides of this invention may be characterized as having recurring group of the structure:

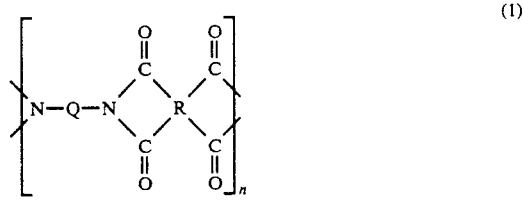

(1)

wherein n is the number of repeating groups, R is a tetravalent organic radical having at least 4 carbon atoms, Q is

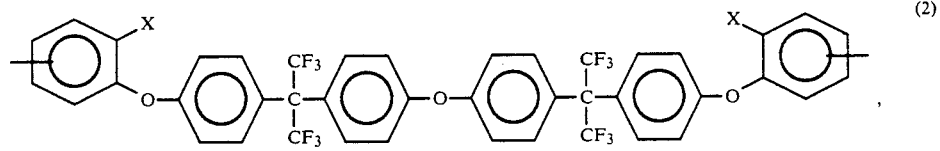

(2)

and X is hydrogen or halogen, preferably hydrogen.
Preferably Q is

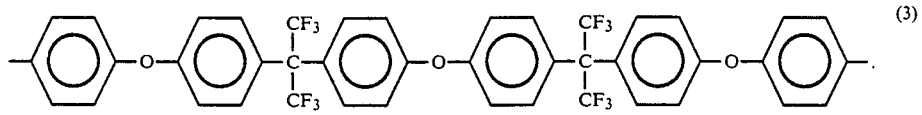

These polyimides are prepared by reacting tetracarboxylic acids or derivatives thereof such as esters or dianhydrides and a diamine of the formula:

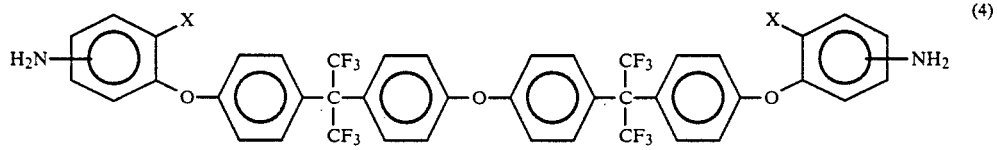

When the amino group is in the meta position on the phenyl ring in relation to the ether linking group, X is hydrogen. When the amino group is in the para position, X may be hydrogen or halogen. The preferred halogen is chlorine. The preferred diamine is

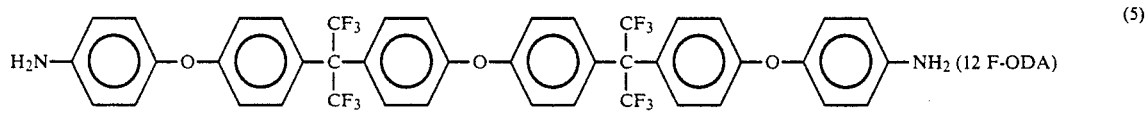

EXAMPLE 1

Preparation of 4,4'-bis[2-(4-Aminophenoxyphenyl) Hexafluoroisopropyl] Diphenyl Ether 4,4'-bis[2-(4-hydroxyphenyl)hexafluoroisopropyl] diphenyl ether is prepared by charging a stainless steel pressure vessel with 4,4'-bis(2-hydroxy-hexafluoroisopropyl) diphenyl ether, phenol and hydrogen fluoride in a molar ratio of at least 1:2:10 and heating to temperatures of between 100° to 170° C. for 24 to 96 hours while stirring. After removing hydrogen fluoride by evaporation, the solid residue is dissolved in ethanol and purified by refluxing in the presence of charcoal. From the filtered solution, a white crystalline precipitate is obtained having a melting point of 179°–180° C.

A 2,000 ml round bottom flask equipped with stirrer, thermometer, condensor, and a nitrogen blanket is charged with 765 ml of dimethyl sulfoxide and 200 g of 4,4'-bis[ 2-(4-hydroxyphenyl) hexafluoroisopropyl] diphenyl ether. The mixture is dissolved at room temperature resulting in a brown solution. Over a five minute period, 39.75 g of sodium methoxide anhydrous powder is added to form a disodium salt. The mixture is stirred for about one hour without temperature control. A solution of 106 g of 1-chloro-4-nitrobenzene in 250 ml of dimethyl sulfoxide is added over a period of about one half hour. The reaction mixture is heated to 100° C. and maintained at this temperature for about 20 hours and then allowed to cool. The reaction solution is then transferred to a 4 liter beaker. While stirring, 600 ml of methanol is dropwise added to the solution followed by the dropwise addition of 250 ml of distilled water to promote crystallization. The crystallized precipitate is filtered, washed with distilled water, and dried overnight in a vacuum oven at 60° C. The yield is 315 g of partially dried crude 4,4'-bis[2-(4-nitrophen-yl)-hexafluoroisopropyl] diphenyl ether.

A 2000 ml erlenmeyer flask is charged with the 315 g of the crude reaction product and 410 ml of acetone. The mixture is heated to dissolve the crude product and then clarified. 700 ml of isopropanol is added to the hot solution. The solution is cooled to 10° C. and the precipitate is filtered and washed with isopropanol. The yield is 190.6 g of the dinitro compound when dried.

A 500 ml PARR bottle is charged with 300 ml of ethyl acetate, 86 g of the dinitro compound and 5 g of 3% Pd/carbon catalyst. The bottle is purged with nitrogen and then placed in a hydrogenation apparatus. The bottle is then purged twice with hydrogen. Under agitation, the reaction mixture is heated to and maintained at about 70° C. and maintained under about 70 psi of hydrogen for about one and a half hours when hydrogen uptake is stopped. It is then allowed to cool to room temperature. The catalyst is filtered off and washed with 20 ml of ethyl acetate. The ethyl acetate is then evaporated leaving 92.5 g of a crude syrup. The syrup is dissolved in 175 ml of isopropanol. 15 g of 32% HCl is dropwise added to the solution to form the amine hydrochloride. The mixture is cooled to 10° C. and the precipitate is filtered, washed with 50 ml of isopropanol, and dried. The amine hydrochloride is then reslurried in 3000 ml of distilled water and the pH is adjusted to 11 with about 5 g of 50% sodium hydroxide. While maintaining the pH at 11, the slurry is stirred overnight to form the free diamine. The diamine is filtered off, washed with 100 ml of distilled water, and dried in a vacuum oven. The yield is 73.8 g of dry 4,4'-bis[2-(4-aminophenoxyphenyl)hexafluoroisopropyl] diphenyl ether (about 90 percent yield from the dinitro compound).

A diamine wherein X is halogen may be obtained by substituting a molar equivalent amount of a 3,4-dihalonitrobenzene such as 129.2 g of 3,4-dichloronitrobenzene for the 1-chloro-4-nitrobenzene in the above procedure.

The diamines of formula (4) may be reacted with tetracarboxylic acids or esters having a formula:

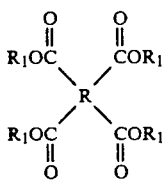   (6)

or with dianhydrides having the formula:

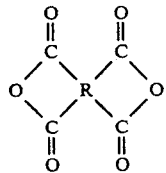   (7)

wherein R is a tetravalent organic radical having at least 4 carbon atoms and $R_1$ is hydrogen or a monavalent organic radical. Preferably R comprises an aromatic moiety such as a phenylene or naphthalene group which may comprise substituent halogen, hydroxy, lower ($C_1$-$C_6$) alkyl or lower ($C_1$-$C_6$) alkoxy groups. Preferably R is selected from the group consisting of

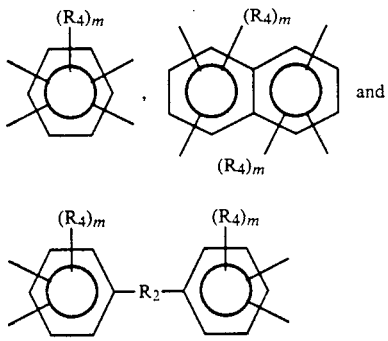

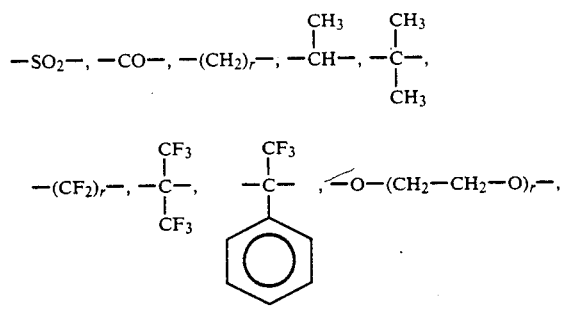

wherein $R_2$ is a carbon-carbon bond, —O—, —S—, —$SO_2$—, —CO—, —($CH_2$)$_r$—,

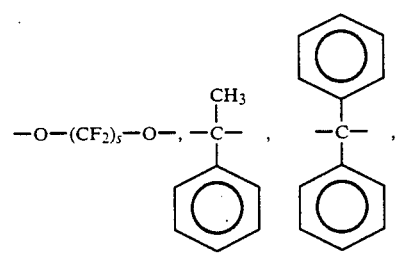

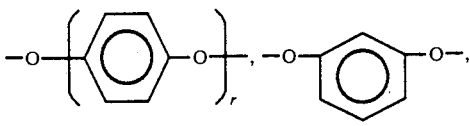

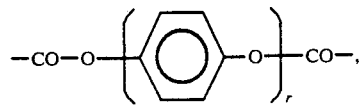

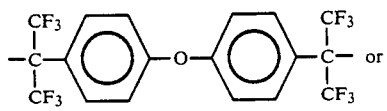

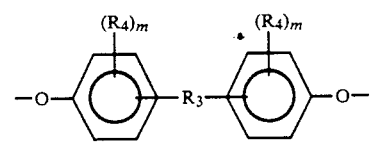

wherein $R_3$ is a carbon-carbon bond, —S—, —$SO_2$—, —CO—, —$CH_2$—, $C_2H_4$—,

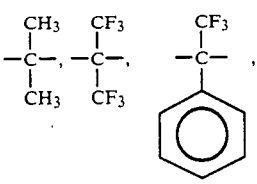

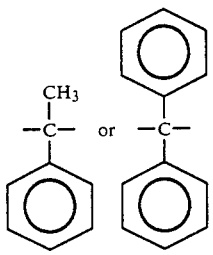

$R_4$ is halogen, hydroxy, lower ($C_1$-$C_6$) alkyl or lower ($C_1$-$C_6$) alkoxy, m is 0 to 2, preferably m is 0, r is 1 to 4, and s is 1 to 5.

Illustrative of tetracarboxylic acid dianhydrides which are suitable for use in the present invention are:
1,2,4,5-benzene tetracarboxylic acid dianhydride;
1,2,3,4-benzene tetracarboxylic acid dianhydride;
1,4-bis(2,3-dicarboxyphenoxy) benzene dianhydride;
1,3-bis(3,4-dicarboxyphenoxy) benzene dianhydride;
1,2,4,5-naphthalene tetracarboxylic acid dianhydride;
1,2,5,6-naphthalene tetracarboxylic acid dianhydride;
1,4,5,8-naphthalene tetracarboxylic acid dianhydride;
2,3,6,7-naphthalene tetracarboxylic acid dianhydride;
2,6-dichloronaphthalene-1,4,5,8-tetracarboxylic acid dianhydride;
2,7-dichloronaphthalene-1,4,5,8-tetracarboxylic acid dianhydride;
2,3,6,7-tetrachloronaphthalene-1,4,5,8-tetracarboxylic acid dianhydride;
3,3',4,4'-diphenyl tetracarboxylic acid dianhydride;
2,2',3,3'-diphenyl tetracarboxylic acid dianhydride;
4,4'-bis(3,4-dicarboxyphenoxy)diphenyl dianhydride;
bis(2,3-dicarboxyphenyl) ether dianhydride;

4,4'-bis(2,3-dicarboxyphenoxy) diphenyl ether dianhydride;
4,4'-bis(3,4-dicarboxyphenoxy) diphenyl ether dianhydride;
bis(3,4-dicarboxyphenyl) sulfide dianhydride;
4,4'-bis(2,3-dicarboxyphenoxy) diphenyl sulfide dianhydride;
4,4'-bis(3,4-dicarboxyphenoxy) diphenyl sulfide dianhydride;
(3,4-dicarboxyphenyl) sulfone dianhydride;
4,4'-bis(2,3-dicarboxyphenoxy) diphenyl sulfone dianhydride;
4,4'-bis(3,4-dicarboxyphenoxy) diphenyl sulfone dianhydride;
3,3',4,4'-benzophenone tetracarboxylic acid dianhydride;
2,2',3,3'-benzophenone tetracarboxylic acid dianhydride;
2,3,3',4'-benzophenone tetracarboxylic acid dianhydride;
4,4'-bis(3,4-dicarboxyphenoxy) benzophenone dianhydride;
bis(2,3-dicarboxyphenyl)methane dianhydride;
bis(3,4-dicarboxyphenyl)methane dianhydride;
1,1-bis(2,3-dicarboxyphenyl)ethane dianhydride;
1,1-bis(3,4-dicarboxyphenyl)ethane dianhydride;
1,2-bis(3,4-dicarboxyphenyl)ethane dianhydride;
2,2-bis(2,3-dicarboxyphenyl)propane dianhydride;
2,2-bis(3,4-dicarboxyphenyl)propane dianhydride;
2,2-bis[4-(2,3-dicarboxyphenoxy)phenyl]propane dianhydride;
2,2-bis[4-(3,4-dicarboxyphenoxy)phenyl]propane dianhydride;
4-(2,3-dicarboxyphenoxy)-4'-(3,4-dicarboxyphenoxy)-diphenyl-2,2propane dianhydride;
2,2-bis[4-(3,4-dicarboxyphenoxy-3,5-dimethyl)phenyl]-propane dianhydride;
1,2,3,4-butane tetracarboxylic acid dianhydride;
1,2,3,4-cyclopentane tetracarboxylic acid dianhydride;
2,3,4,5-thiophene tetracarboxylic acid dianhydride;
2,3,4,5-pyrrolidine tetracarboxylic acid dianhydride;
2,3,5,6-pyrazine tetracarboxylic acid dianhydride;
1,8,9,10-phenanthrene tetracarboxylic acid dianhydride;
3,4,9,10-perylene tetracarboxylic acid dianhydride;
2,2-bis(3,4-dicarboxyphenyl) hexafluoropropane dianhydride;
1,3-bis(3,4-dicarboxyphenyl)hexafluoropropane dianhydride;
1,1-bis(3,4-dicarboxyphenyl)-1-phenyl-2,2,2-trifluoroethane dianhydride;
2,2-bis[4-(3,4-dicarboxyphenoxy)phenyl]hexafluoropropane dianhydride;
1,1-bis[4-(3,4-dicarboxyphenoxy)phenyl]-1-phenyl-2,2,2-trifluoroethane dianhydride;
and mixtures thereof.

A mixture of at least two suitable tetracarboxylic acids or derivatives thereof may be reacted with a diamine of formula (4) to produce copolyimides.

One skilled in the art will recognize that the tetracarboxylic acids and acid-esters of the above-listed dianhydride compounds may also be used to produce the polyimides. These tetracarboxylic acids or derivatives thereof are available or may be prepared by known methods. For example, U.S. Pat. No. 3,847,867 to Heath et al. and U.S. Pat. No. 4,650,850 to Howson, which are incorporated herein by reference, show the preparation of bis(ether anhydrides)) and bis(dialkyl aromatic ether anhydrides)), respectively. The preparation of fluorine-containing dianhydrides is disclosed in U.S. Patent No. 3,310,573 to Gordon and U.S. Pat. No. 3,649,601 to Critchley et al., which are also incorporated herein by reference.

Preferred polyimides are those prepared from the diamine of formula (5) and dianhydrides of the formula:

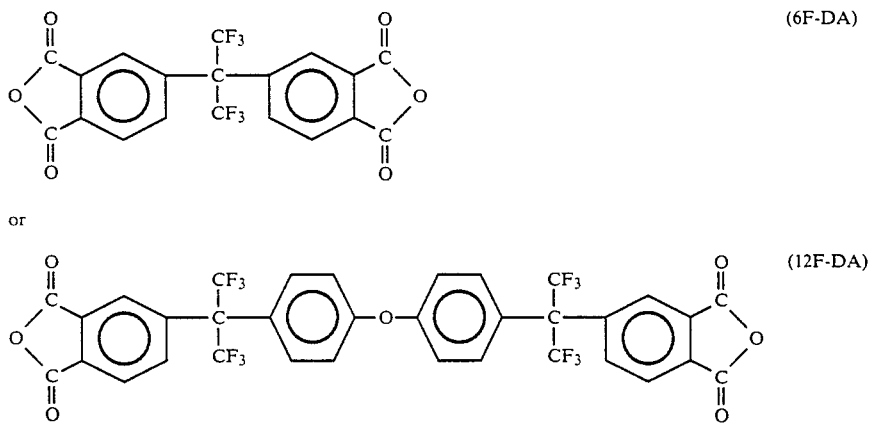

The 12F-DA dianhydride may be prepared in the following manner:

EXAMPLE 2

Preparation of 4,4'-bis[2-(3,4-Dicarboxyphenyl) Hexafluoroisopropyl] Diphenyl Ether Dianhydride To a stainless steel reactor 4,4'-bis(2-hydroxyhexafluoroisopropyl) diphenyl ether, o-xylene and hydrogen fluoride are charged in a molar ratio of at least 1:2:10. The reaction mixture is stirred in the closed reactor under autogenous pressure at temperatures of between 100° and 1700° C. for 24 to 96 hours. After evaporation of the hydrogen fluoride at 80° C., the contents of the reactor are poured into ice. The formed organic layer is separated, diluted with methylene chloride, and dried over calcium chloride. After evaporation of the solvent, the crude product is treated with charcoal in chloroform, filtered and recrystallized. The 4,4'-bis[2-(3,4-dimethylphenyl) hexafluoroisopropyl]-diphenyl ether has a melting point 139°–141° C. The thusly obtained diphenyl ether is dissolved in acetic acid and charged in to a glass pressure vessel. A catalytic amount of a solution of Co(OAc)$_2$.4H$_2$O, Mn(OAc)$_2$.4 H$_2$O, HBr and acetic acid is added. The reaction mixture is heated up to 180° C. under an oxygen pressure of 7.5 bar. The exothermic reaction starts at about 90° C. with oxygen uptake and is finished in 2 hours at 180° C. The reaction product is then treated with a small amount of oxalic acid dihydrate in acetic acid. After heating the mixture to reflux temperature for 2 hours, the solution is filtered. Acetic acid and water are distilled off. Acetic acid anhydride is added to the residue and the solution is heated to 120° C. for one hour. After cooling to room temperature, the crystalline product is isolated, washed three times with a mixture of acetic acid and its anhydride, and dried in vacuo yielding 4,4'-bis[2-(3,4-dicarboxyphenyl) hexafluoroisopropyl] diphenyl ether dianhydride. M.P. 168°–170° C.

A preferred process for preparing the polyimides of this invention involves first preparing a polyamide-acid by reacting the diamine and the tetracarboxylic acid or derivative such as the dianhydride in an organic solvent, preferably under substantially anhydrous conditions for a time and at a temperature sufficient to provide at least 50% of the corresponding polyamide-acid, and then converting the polyamide-acid to the polyimide. Suitable conditions for reacting the diamine and the dianhydride are disclosed in detail in U.S. Pat. Nos. 3,356,648 and 3,959,350, both to Rogers, which are incorporated herein by reference. The intermediate polyamide-acid may also be esterified to provide polyamide-esters.

The polyamide-acids/esters are characterized by the formula:

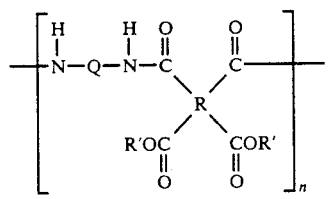

(8)

wherein n is the number of repeating groups, R is a tetravalent organic radical as defined above, R' is hydrogen or a monovalent organic radical, and Q is a divalent radical as defined in formula (2). Preferably, Q has the structure of formula (3). In addition to being useful to produce polyimides, the polyamide-acids may be esterified with thermally polymerigable or photopolymerizable compounds such as olefinically unsaturated monoepoxides to produce polyamide-esters useful in photoresist compositions.

The polyamide-acids/esters may be cyclicized to form polyimides. Conversion to the polyimides may be accomplished by a heat treatment, a chemical treatment or both as described in the above-referenced Rogers patents.

In a preferred process for preparing the polyimides, the diamine and dianhydride are reacted in gamma-butyrolactone (BLO), or a mixture of BLO and another solvent such as diglyme. The resulting product is a polyamide-acid which is then converted to the desired polyimide by one of several methods: heating the polyamide-acid solution until imidization is substantially complete; or by combining the polyamide-acid solution and a dehydrating agent, with or without catalyst, and optionally heating the resulting mixture until imidization is substantially complete. The use of the BLO solvent provides several advantages in that it avoids the formation of complexes of the polyamide-acid and the solvent that typically occur when solvents such as N-methyl pyrrolidone (NMP) are used and allows the removal of the solvent to proceed at lower temperatures (below 250° C.) to obtain a substantially uniform films. When mixed with diglyme, the ratio by volume of BLO to diglyme is preferably in the range of about 10:90 to 90:10, more preferably of about 40:60 to 60:40.

The following examples are illustrative of the invention:

EXAMPLE 3

To a 250 ml reaction unit fitted with a condenser, thermometer, stirrer and nitrogen blanket, and purged with nitrogen, 16.72 g (0.02 moles) of 4,4'bis[2-(4-aminophenoxyphenyl)hexafluoroisopropyl] diphenyl ether (hereinafter "12F-ODA") are charged along with 50 g of distilled N-methyl pyrrolidone (NMP) under nitrogen atmosphere. The mixture is stirred to get a clear solution. To the clear, very pale yellow color solution, 15.24 g (0.02 moles) of 4,4'-bis[2-(3,4-dicarboxyphenyl) hexafluoroisopropyl] diphenyl ether dianhydride (hereinafter "12F-DA") are charged while stirring is continued. 78 g of NMP is added to the reaction mixture which is then stirred overnight at room temperature. The resulting polyamic acid has an inherent viscosity of 0.60 dl/g, measured at 0.5 g/dl at 25° C. in dimethyl acetamide (DMAc). 36.00 g of acetic anhydride and 3.60 g of 3-picoline are added to 140 g of the polyamic acid solution. The reaction is stirred at room temperature for about six hours and the resulting polyimide is precipitated in methanol, isolated by filtration, washed with fresh methanol, and dried overnight in a vacuum oven at 85° C. It is soluble in acetone, DMAc, diglyme, MEK, NMP, THF, chloroform, BLO solvents.

A film is prepared from a solution comprising 20% by weight solids in a 50/50 mixture by volume of BLO/diglyme and cured to 350° C. by stepwise heating. A very pale yellow, clear, flexible, self-supporting, tough film is obtained. Its glass transition temperature ($T_g$) is 222° C. by differential scanning calorimetry (DSC) and 5% weight loss is at 527° C. by thermal gravimetric analysis (TGA). Tensile strength is about 11800 psi at room temperature. Tensile modulus is about 284 Ksi at room temperature, elongation at break is about 9% at room temperature, and it has a limiting oxygen index of 46. The dielectric constant, measured on a Hewlett Packard Automated Network Analyzer at ambient temperature over a frequency range of 8–12 GHz, is 2.45.

EXAMPLE 4

To a 250 ml reaction unit fitted with a condenser thermometer, stirrer and nitrogen blanket, and purged with nitrogen, 12.54 g (0.015 moles) of 4,4'bis[2-(4-aminophenoxyphenyl)hexafluoroisopropyl] diphenyl ether (hereinafter "12F-ODA") are charged along with 40 g of distilled N-methyl pyrrolidone (NMP) under nitrogen atmosphere. The mixture is stirred to get a clear solution. To the solution, 6.66 g (0.015 moles) of 2,2'-bis(3, 4-dicarboxyphenyl)hexafluoropropane dianhydride (hereinafter "6F-DA") are charged while stirring is continued. 36.8 g of NMP are added to the reaction mixture which is then stirred overnight at room temperature. The resulting polyamic acid has an inherent viscosity of 0.62 dl/g, measured at 0.5 g/dl at 25° C. in dimethyl acetamide (DMAc). 22 g of acetic anhydride and 2.2 g of 3-picoline are added to 85 g of the polyamic acid solution. The reaction is stirred at room temperature for about six hours and the resulting polyimide is precipitated in methanol, isolated by filtration, washed with fresh methanol, and dried overnight in a vacuum oven at 85° C. It is soluble in acetone, DMAc, diglyme, MEK, NMP, THF, chloroform, BLO solvents.

A film is prepared from a solution comprising 15% by weight solids in a 50/50 mixture by volume of BLO/diglyme and cured to 350° C. by stepwise heating. A very pale yellow, clear, flexible, self-supporting, tough film is obtained. Its glass transition temperature ($T_g$) is 226° C. by differential scanning calorimetry (DSC) and 5% weight loss is at 525° C. by thermal gravimetric analysis (TGA). Tensile strength is about 11100 psi at room temperature. Tensile modulus is about 296 Ksi at room temperature, elongation at break is about 11% at room temperature, and it has a limiting oxygen index of 46. The dielectric constant, measured on a Hewlett Packard Automated Network Analyzer at ambient temperature over a frequency range of 8–12 GHz, is 2.46.

EXAMPLES 5–8

Polyimides are prepared in accordance with the procedure set forth in Example 3 by reacting the 12F-ODA diamine with the following dianhydrides:
1,2,4,5-benzene tetracarboxylic acid dianhydride (PMDA),
3,3',4,4'-diphenyl tetracarboxylic acid dianhydride (BPDA),
3,3',4,4'-benzophenone tetracarboxylic acid dianhydride (BTDA),
and bis(3,4-dicarboxyphenyl) ether dianhydride (ODPA).

The properties of the resulting polyimides are shown in Table 1.

TABLE 1

| Dianhydride | Units | Example Number | | | |
|---|---|---|---|---|---|
| | | 5 PMDA | 6 BPDA | 7 BTDA | 8 ODPA |
| Ratio of 12F-ODA/ Dianhydride | millimole/ millimole | 20/20 | 20/20 | 20/20 | 15/15 |
| Inherent Viscosity (Polyamic Acid) | dl/g at 25° C. in DMAc | 0.93 | 0.77 | 0.72 | 0.88 |
| Inherent Viscosity (Polyimide) | dl/g at 25° in DMAc | — | 0.66 | 0.62 | 0.71 |
| Glass Transition Temp. (Tg) | °C. | 260 | 240 | 227 | 242 |
| 5% Weight loss in air (TGA) | °C. | 520 | 520 | 530 | 520 |
| Tensile Strength at room temp. | psi | 7,800 | 15,500 | 11,800 | 12,000 |
| Tensile Modulus at room temp. | Ksi | 240 | 330 | 350 | 330 |
| Elongation at break | % | 15.2 | 9.8 | 6.5 | 7.7 |

The polyimides exhibit good solubility properties in solvents such as N-methyl pyrrolidone (NMP) dimethyl acetamide (DMAc), diglyme, methylethylketone (MEK), tetrahydrofuran (THF), acetone, chloroform, butyrolactone (BLO), dimethylsulfoxide (DMS), dimethylformamide (DMF) and the like.

The polyimides of this invention may be molded using standard techniques such as compression molding or injection molding to produce melt fabricated articles such as safety masks, windshields, electronic circuit substrates, airplane windows or the like. They may be compounded with graphite, graphite fiber, molybdenum disulphide or PTFE for the production of self-lubricating wear surfaces useful for piston rings, valve seats, bearings and seals. They may also be compounded with fibers such as glass, graphite or boron fibers to produce molding compounds for high strength structural components such as jet engine components. The polyimides may also be compounded with friction materials to produce molding compounds for high temperature braking components or with abrasive materials such as diamonds for high speed grinding wheels.

The polyimides may be cast as films useful as wire and cable wraps, motor slot liners or flexible printed circuit substrates. They may be used as coatings on substrates such as aluminum or silicone dioxide. They are also useful to produce high temperature coatings for magnetic wire, dip coatings for various electronic components, protective coatings over glass, metal and plastic substrates, wear coatings, and photoresist coatings useful in microelectronic processing.

The polyimides may also be used to produce high temperature adhesives for bonding aerospace structures or electrical circuitry, conductive adhesives when mixed with conductive fillers such as silver or gold for microelectronic applications, or adhesives for glass, metal or plastic substrates.

They may be used as varnish compositions or matrix resins to produce composites and laminates. The varnish compositions and matrix resins may be used to impregnate glass or quartz cloth, or graphite or boron fibers, for the production of radomes, printed circuit boards, radioactive waste containers, turbine blades, aerospace structural components or other structural components requiring high temperature performance, non-flammability and excellent electrical properties.

The polyamides of this invention may be characterized as having recurring groups of the structure:

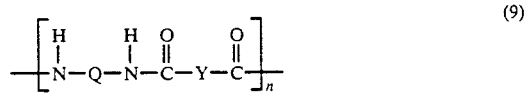
(9)

wherein n is the number of repeating groups, Y is a divalent organic radical, and Q is a divalent radical as defined in formula (2). Preferably, Q has the structure of formula (3).

The polyamides are prepared by reacting an acid chloride of dicarboxylic acids and a diamine of formula (4). The dicarboxylic acids have the general formula:

$$XOOC—Y—COOX \quad (10)$$

wherein X is hydrogen or halogen, Y is a divalent organic radical, preferably containing an aromatic moiety. Preferably, Y is selected from the group consisting of

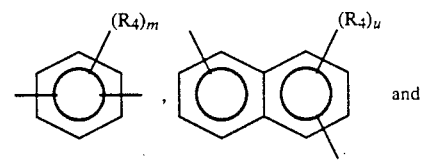
and

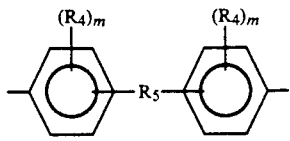

wherein R$_5$ is a carbon-carbon bond, —O—, —S—, —SO$_2$—, —CO—, —(CH$_2$)$_r$—,

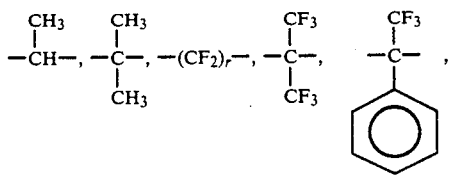

—O—(CH$_2$—CH$_2$—O)$_r$—, —O—(CF$_2$)$_s$—O—,

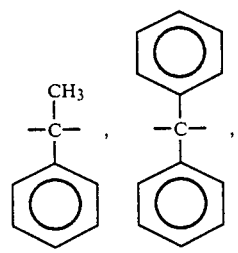

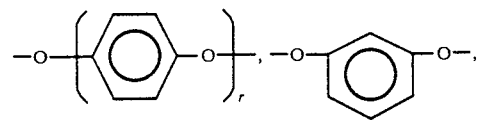

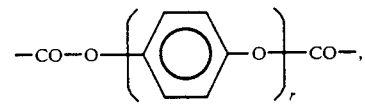

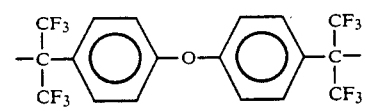

or

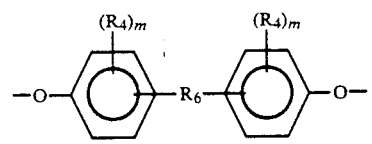

wherein R$_6$ is a carbon-carbon bond, —S—, —SO$_2$—, —CO—, —CH$_2$—, —C$_2$H$_4$—,

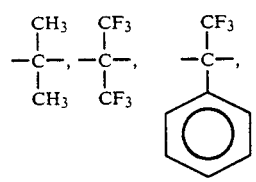

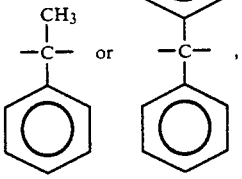

R$_4$ is halogen, hydroxy, lower (C$_1$–C$_6$) alkyl, or lower (C$_1$–C$_6$) alkoxy, m is 0 to 4, preferably m is 0, r is 1 to 4, s is 1 to 5, and u is 0 to 6, preferably u is 0.

Illustrative of dicarboxylic acids which are suitable for use in the present invention are:
phthalic acid;
isophthalic acid;
terephthalic acid;
biphenyl-3,3'-dicarboxylic acid;
biphenyl-4,4'-dicarboxylic acid;
bis(3-carboxyphenyl)methane;
bis(4-carboxyphenyl)methane;
2,2-bis(3-carboxyphenyl)propane;
2,2-bis(4-carboxyphenyl)propane;
naphthalene-2,6-dicarboxylic acid;
bis(3-carboxyphenyl)ether;
bis(4-carboxyphenyl)ether;
bis(3-carboxyphenyl)sulfide;
bis(4-carboxyphenyl)sulfide;
bis(3-carboxyphenyl)sulfone;
bis(4-carboxyphenyl)sulfone;
1,4-cyclohexane dicarboxylic acid;
pentanedioic acid;
hexanedioic acid;
1,4-phenylene diethanoic acid;
2,4-furandicarboxylic acid;
1,4-bis(4-carboxyphenoxy)phenylene;
1,1-bis(4-carboxyphenyl)-1-phenyl-2,2,2-trifluoroethane;
bis-(4-carboxyphenyl)-methyl phosphane oxide;
4,4'-dicarboxyltetraphenyl silane;
5-tertiary butyl isophthalic acid;
5-bromoisophthalic acid;
5-chloroisophthalic acid;
5-fluoroisophthalic acid;
2,2-bis(4-carboxyphenyl)hexafluoropropane;
2,2-bis[4-(4-carboxy-phenoxy)phenyl]hexafluoropropane;
1,1-bis[4-(4-carboxyphenoxy)phenyl]-1-phenyl-2,2,2-trifluoroethane;
and mixtures thereof.

A mixture of at least two dicarboxylic acids may be reacted with a diamine of formula (4) to produce copolyamides.

Preferred polyamides are those prepared from the diamine of formula (5) and the acid chlorides of 2,2-bis(4-carboxyphenyl)hexafluoropropane or the dicarboxylic acid of the formula:

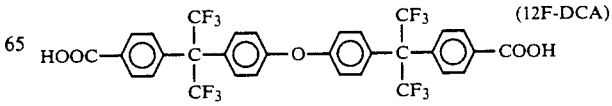 (12F-DCA)

The synthesis of 2,2-bis(4-carboxyphenyl) hexafluoropropane and its corresponding diacid chloride is described in U.S. Pat. No. 3,328,352 to Kwolek, which is incorporated herein by reference.

The 12F-DCA dicarboxylic acid may be prepared in the following manner:

EXAMPLE 9

Preparation of 4,4'-bis[2-(4-Carboxyphenyl) Hexafluoroisopropyl]Diphenyl Ether

To a clean, dry stainless steel autoclave are charged 4,4'-bis(2-hydroxy-hexafluoroisopropyl)diphenyl ether, toluene and hydrogen fluoride in a molar ratio of at least 1:2:10 followed by and heating at temperatures of between 100° and 170° C. for to 96 hours. The autoclave is then vented at 80° C. and hydrogen fluoride is evaporated. After cooling to room temperature, methylene chloride is added and the reaction mixture is discharged into water. The organic layer is separated, washed twice with water, and dried over calcium chloride. The solvent is stripped off and the residue is recrystallized from ethanol yielding 4,4'-bis[2-(4-methylphenyl)hexafluoroisopropyl]diphenyl ether. M.P. 89°–90° C.

4,4'-bis[2-(4-methylphenyl)hexafluoroisopropyl]-diphenyl ether is dissolved in acetic acid. A catalyst prepared from $Co(OAc)_2.4 H_2O$, $Mn(OAc)_2.4 H_2O$ and HBr in acetic acid is then added. The reaction is performed in a glass pressure vessel by heating the mixture up to 180° C. under oxygen at a pressure of 6.5 bar. After the oxygen uptake has finished, the contents of the reaction vessel are discharged into a distillation apparatus and acetic acid is distilled off. The residue is cooled to room temperature and the crystalline product is collected in a funnel filter. After washing several times with acetic acid and water, the 4,4'-bis[2-(4-carboxyphenyl)hexafluoroisopropyl]diphenyl ether is dried in vacuo. M.P. 238°–240° C.

The acid chloride is obtained by adding a few drops of dimethylformamide to a slurry of 4,4'-bis[2-(4-carboxyphenyl)hexafluoroisopropyl]diphenyl ether in thionylchloride. The mixture is heated at reflux until the evolution of hydrogen chloride stops. The excess thionylchloride is stripped off. Toluene is added to remove the residual thionylchloride by distillation. The solvent is stripped off and the crude product is recrystallized from n-hexane. The resulting acid chloride has a melting point of 145°–146° C.

The polyamides of this invention may be prepared by interfacial or solvent polymerization by reacting the diamine such as 12F-ODA with a diacid chloride at low temperatures (below 100° C.) These processes are described in detail in U.S. Pat. No. 2,831,834 to Magat and U.S. Pat. No. 3,063,966 to Kwolek et al., which are incorporated herein by reference.

The following examples illustrate the invention. Unless otherwise indicated, the inherent viscosity reported in the examples is determined in dimethyl acetamide at 25° C. at a 0.5 g/dl concentration.

EXAMPLE 10

Into a blender is placed 37.5 ml of water, 37.5 ml of tetrahydrofuran; 4.18 g (0.005 moles) of 12F-ODA, 1.06 g of sodium bicarbonate and 0.1 g of benzyltriethyl ammonium chloride. The contents of the blender are stirred rapidly for 5 minutes. A solution of 1.015 g (0.005 moles) of isophthaloyl chloride in 22.5 ml of tetrahydrofuran is added over a period of 3 minutes. An emulsion is formed which is stirred for ten minutes. Thereafter 300 ml of water are added to precipitate the polymer. This mixture is stirred for additional ten minutes, filtered in a buchner funnel, washed with water, and dried in vacuum overnight at 90°–100° C. The yield of the polymer is nearly quantitative. The inherent viscosity of the polymer is 0.76 dl/g in dimethyl acetamide (0.5% at 25° C.) and it has a glass transition temperature (Tg) of 221° C.

EXAMPLES 11–17

The polyamides shown in Table 2 are prepared in accordance with the procedure set forth in Example 9 by reacting 0.005 moles of the 12F-ODA diamine with the following diacid chlorides:

TABLE 2

| Example Number | Diacid(s) | Inherent Viscosity (dl/g) | Glass Transit Temperature (°C.) |
|---|---|---|---|
| 11 | 2,2-bis(4-chlorocarbonylphenyl)-hexafluoropropane (0.005 moles) | 0.98 | 240 |
| 12 | 4,4'-bis[2-(4-chlorocarbonylphenyl)-hexafluoroisopropyl]-diphenyl ether (0.005 moles) | 0.27 | 191 |
| 13 | oxydiphthaloyl chloride (0.005 moles) | | |
| 14 | 1,4-bis(4-chlorocarbonylphenoxy)-benzene (0.005 moles) | | |
| 15 | napthalene-2,6-dicarbonyl chloride (0.005 moles) | | |
| 16 | isophthaloyl chloride (0.0025 moles) and terephthaloyl chloride (0.0025 moles) | | |
| 17 | terephtaloyl chloride (0.005 moles) | | |

The polyamides of this invention are especially useful for the shaping of films and fibers. The polyamides are also useful in coatings and coating compositions. It has been found that these polyamides have low glass transition temperatures and high solubilities in solvents such as dimethylacetamide, N-methyl pyrrolidone, methyethylketone, tetrahydrofuran, butyrolactone and the like. This combination of properties greatly facilitates film casting or dry spinning from solutions of such polyamides and permits orientation drawing of the film or fiber at relatively low temperatures.

The invention also provides new copolyamides, copolyamide-acids/esters, and copolyimides. The copolymers are prepared by reacting dicarboxylic acids or tetracarboxylic acids or derivatives thereof with a mixture of at least one diamine of formula (4) and at least one diamine having the formula:

$$H_2N-A-NH_2 \quad (11)$$

wherein A is a divalent organic radical, preferably containing an aromatic moiety. Preferably A is selected from the group consisting of

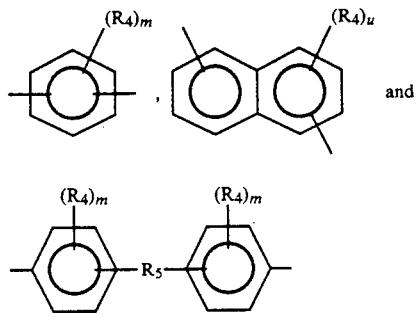

wherein $R_5$ is a carbon-carbon bond, —O—, —S—, —SO$_2$—, —CO—, —(CH$_2$)$_r$—,

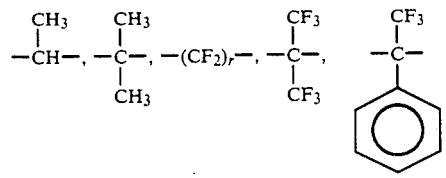

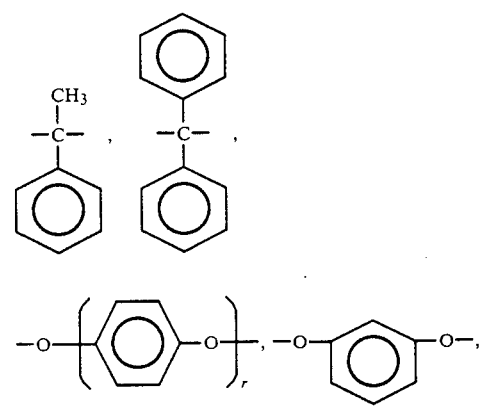

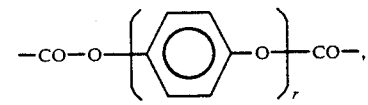

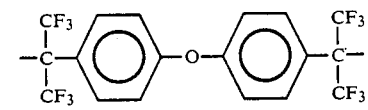

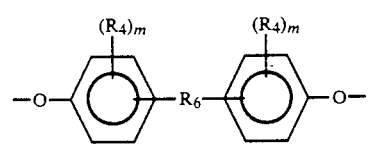

wherein $R_6$ is a carbon-carbon bond, —S—, —SO$_2$—, —CO—, —CH$_2$—, —CH$_2$H$_4$—,

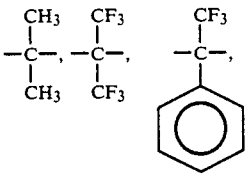

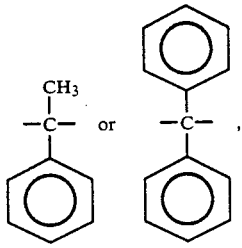

$R_4$ is hydrogen, hydroxy, lower (C$_1$–C$_6$) alkyl, or lower (C$_1$–C$_6$) alkoxy, m is 0 to 4, preferably m is 0, r is 1 to 4, s is 1 to 5, and u is 0 to 6, preferably u is 0.

Illustrative of diamines which are suitable for use in the present invention are:
m-phenylene diamine;
p-phenylene diamine;
1,3-bis(4-aminophenyl) propane;
2,2-bis(4-aminophenyl) propane;
4,4'-diamino-diphenyl methane;
1,2-bis(4-aminophenyl) ethane;
1,1-bis(4-aminophenyl) ethane;
2,2'-diamino-diethyl sulfide;
bis(4-aminophenyl) sulfide;
2,4'-diamino-diphenyl sulfide;
bis(3-aminophenyl) sulfone;
bis(4-aminophenyl) sulfone;
4,4'-diamino-dibenzyl sulfoxide;
bis(4-aminophenyl) ether;
bis(3-aminophenyl) ether;
bis(4-aminophenyl) diethyl silane;
bis(4-aminophenyl) diphenyl silane;
bis(4-aminophenyl) ethyl phosphine oxide;
bis(4-aminophenyl) phenyl phosphine oxide;
bis(4-aminophenyl)-N-phenylamine;
bis(4-aminophenyl)-N-methylamine;
1,2-diamino-naphthalene;
1,4-diamino-naphthalene;
1,5-diamino-naphthalene;
1,6-diamino-naphthalene;
1,7-diamino-naphthalene;
1,8-diamino-naphthalene;
2,3-diamino-naphthalene;
2,6-diamino-naphthalene;
1,4-diamino-2-methyl-naphthalene;
1,5-diamino-2-methyl-naphthalene;
1,3-diamino-2-phenyl-naphthalene;
4,4'-diamino-biphenyl;
3,3'-diamino-biphenyl;
3,3'-dichloro-4,4'-diamino-biphenyl;
3,3'-dimethyl-4,4'-diamino-biphenyl;
3,4'-dimethyl-4,4'-diamino-biphenyl;
3,3'-dimethoxy-4,4'-diamino-biphenyl;
4,4'-bis(4-aminophenoxy)-biphenyl;
2,4-diamino-toluene;
2,5-diamino-toluene;
2,6-diamino-toluene;
3,5-diamino-toluene;

1,3-diamino-2,5-dichloro-benzene;
1,4-diamino-2,5-dichloro-benzene;
1-methoxy-2,4-diamino-benzene;
1,4-diamino-2-methoxy-5-methyl-benzene;
1,4-diamino-2,3,5,6-tetramethyl-benzene;
1,4-bis(2-methyl-4-amino-pentyl)-benzene;
1,4-bis(1,1-dimethyl-5-amino-pentyl)-benzene;
1,4-bis(4-aminophenoxy)-benzene;
o-xylylene diamine;
m-xylylene diamine;
p-xylylene diamine;
3,3'-diamino-benzophenone;
4,4'-diamino-benzophenone;
2,6-diamino-pyridine;
3,5-diamino-pyridine;
1,3-diamino-adamantane;
3,3'-diamino-1,1'-diadamantane;
bis(4-amino-cyclohexyl) methane;
1,5-diamino-pentane;
1,6-diamino-hexane;
1,7-diamino-heptane;
1,8-diamino-octane;
1,9-diamino-nonane;
1,10-diamino-decane;
1,7-diamino-3-methyl-heptane;
1,7-diamino-4,4-dimethyl-heptane;
2,11-diamino-dodecane;
1,3-bis(3-aminopropoxy) ethane;
1,3-diamino-2,2-dimethyl-propane;
1,6-diamino-3-methoxy-hexane;
1,6-diamino-2,5-dimethyl-hexane;
1,7-diamino-2,5-dimethyl-heptane;
1,9 diamino-5-methyl-nonane;
1,4-diamino-cyclohexane;
2,5-diamino-1,3,4-oxadiazole;
N-(3-aminophenyl)-4-aminobenzamide;
4-aminophenyl-3-aminobenzoate;
2,2-bis(4-aminophenyl) hexafluoropropane;
2,2-bis(3-aminophenyl) hexafluoropropane;
2,2-bis[4-(4-aminophenoxy)phenyl]hexafluoropropane;
2,2-bis[4-(2-chloro-4-aminophenoxy)phenyl]hexafluoropropane;
1,1-bis(4-aminophenyl)-1-phenyl-2,2,2-trifluoroethane;
1,1-bis[4-(4-aminophenoxy)phenyl]-1-phenyl-2,2,2-trifluoroethane;
1,4-bis(3-aminophenyl)buta-1-ene-3-yne;
1,3-bis(3-aminophenyl)hexafluoropropane;
1,5-bis(3-aminophenyl)decafluoropentane; and
mixtures thereof.

Preferably, the molar ratio of diamine of formula (4) to diamine of formula (11) is in the range of from about 10:90 to about 99:1, more preferably of from about 50:50 to about 99:1.

The tetracarboxylic acids and derivatives of formulae (6) and (7) and the dicarboxylic acids of formula (10) are suitable for the preparation of the copolymers of this invention. The copolyimides and copolyamides are useful for the utilities discussed above for the polyimides and polyamides, respectively.

The invention provides new monomers, oligomers, prepolymers and the corresponding addition polyimides prepared therefrom. The monomers, oligomers and prepolymers are prepared by reacting the diamines of formula (4), or the precursor condensation product of the diamines of formula (4) and the tetracarboxylic acids or derivatives of formulae (6) or (7), with reactive end-capping compounds such as vinyl aromatic anhydrides, nadic acids or derivatives thereof such as anhydrides or acid-esters, maleic anhydrides, aromatic ethynyl amines, or benzocyclobutene amines.

The monomers, oligomers and prepolymers are useful for adhesive compositions, coating compositions, laminate varnish compositions, and composite matrix resin compositions. They may be reacted by addition polymerization reactions to provide addition polyimides which are useful for coatings, laminates and composites.

One class of addition-type polyimide prepolymers may be characterized as having the following structure:

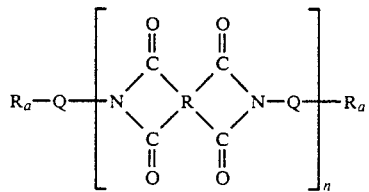
(12)

wherein n is 0 to 4, R is a tetravalent organic radical as defined above, Q is a divalent radical as defined in formula (2), $R_a$ is

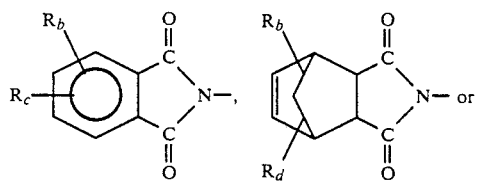

$R_b$ is hydrogen, halogen preferably fluorine, or lower ($C_1$-$C_3$) alkyl preferably methyl, $R_c$ is

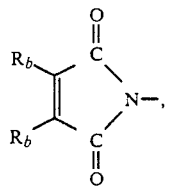

Z is —$(CH_2)_t$—, t is 0 to 4, $R_d$ is H or $R_c$, and $R_e$ is H or $CH_3$.

Preferably, Q has the structure of formula (3), $R_b$ is hydrogen, $R_d$ is hydrogen, n is 0 or 1, and t is 0 or 1.

Preferably, $R_a$ is

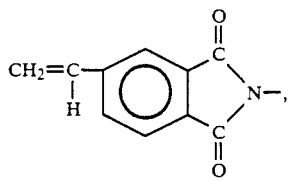

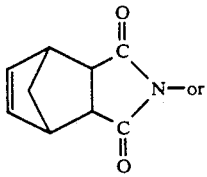 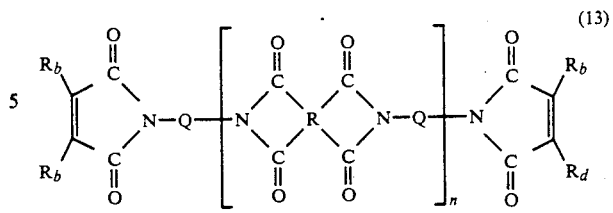

(13)

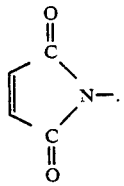

Generally speaking, this class of prepolymers may be prepared by reacting dicarboxylic acids, wherein the carboxyl groups are linked to adjacent carbon atoms, or derivatives thereof such as acid-esters or anhydrides, wherein n is 0 to 4, and R, Q, and $R_b$ are the radicals as defined above. Preferably, Q has the structure of formula (3), $R_b$ is hydrogen or fluorine, and n is 0 or 1. The preferred end-capping agents are maleic anhydride and difluoromaleic anhydride.

The preparation of bisnadimide prepolymers and the corresponding addition polyimides is generally shown in U.S. Pat. No. 3,528,950 to Hyman, which is incorporated herein by reference. The bisnadimides of the present invention may be characterized as having the structure:

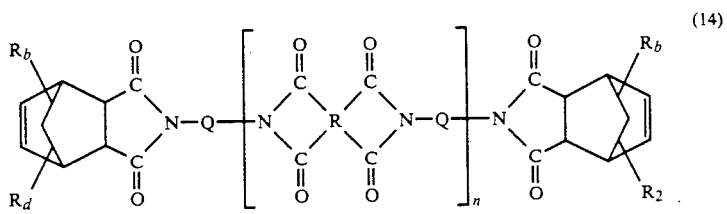

(14)

wherein n is 0 to 4, and R, Q, $R_b$ and $R_d$ are radicals as defined above. Preferably, Q has the structure of formula (3), $R_b$ is hydrogen or methyl, Rd is hydrogen, and n is 0 or 1. The preferred end-capping agent is 5-norbornene-2,3-dicarboxylic acid anhydride.

Another method of preparing addition polyimides and polyimide prepregs using nadic acid compounds is disclosed in U.S. Pat. No. 4,233,258 to St. Clair, U.S. Pat. No. 4,281,102 to St. Clair et al., and Johnston et al., "A Mechanistic Study of Polyimide Formation from Diester-Diacids," Journal of Polymer Science: Part A: Polymer Chemistry, Vol. 25, pp. 2175-2183 (1987), which are incorporated herein by reference. According to this approach a diamine, a nadic acid-ester, and a tetracarboxylic diacid-diester are dissolved in a lower alkyl alcohol such as a methanol or ethanol. The nadic acid-ester and tetracarboxylic diacid-diester may be made by refluxing stoichiometric amounts of the nadic anhydride and tetracarboxylic dianhydride with excess alcohol such as ethanol. The resulting solution is cooled to room temperature and the diamine is then added. The homogeneous mixture may then be used for prepregging onto fibers. The polymerization proceeds through two steps. The first step involves heating to cause imidization (120°-230° C.) to occur resulting in limited chain extension to form low molecular weight norborene end-capped oligomers. In the second step, the norborene endcaps are crosslinked by heating to higher temperatures (275°-325° C.). Because this final reaction occurs without the release of volatile materials, high quality void-free composites may be fabricated. Typically, the solvents used in this type of system have been methanol and ethanol. However, it has been found that is is advantageous to use propylene glycol methyl ether (PGME) as a solvent in this system. By using PGME, certain environmental hazards associated with the handling and disposal of solvents such as methanol and with the diamines of formula (4) or with the condensation product of the diamines of formula (4) and the tetracarboxylic acids or derivatives of formulae (6) or (7). The preferred diamine is the 12F-ODA diamine of formula (5). The preferred end-capping compounds are vinyl-substituted ortho-phthalic acid anhydrides, nadic acid anhydrides and maleic acid anhydrides.

If a dianhydride is to be included in the polymer chain, the diamine may be condensed first with the dianhydride and then the end-capping agent may be reacted with this intermediate condensation product. Alternatively, the diamine may be reacted with a mixture of the dianhydride and end-capping agent. The molar ratio of the diamine to dianhydride must be sufficient to provide terminal amino groups at the ends of the intermediate product for the purpose of reacting the product with the end-capping agent. Generally, the molar ratios of diamine to dianhydride will range from about 2:1 to about 4:3. The preferred dianhydrides are the 6F-DA dianhydride, the 12F-DA dianhydride, the BTDA dianhydride, the ODPA dianhydride, and 2,2-bis[4-(3,4-dicarboxyphenoxy)-phenyl]hexafluoropropane dianhydride.

The preparation of bismaleimides prepolymers and the corresponding addition polyimides is generally shown in U.S. Patent No. 4,173,700 to Green et al., which is incorporated herein by reference. The bismaleimides of the present invention may be characterized as having the structure:

ethanol are avoided. The monomer reactants may be dissolved in up to about a 50 weight percent solution using PGME as a solvent.

The following examples are illustrative of prepolymers and addition polyimides of this invention:

EXAMPLE 18

A four-necked flask fitted with a stirrer and maintained under a nitrogen atmosphere is charged with 8.36 g (0.01 moles) of 12F-ODA, 2.1573 g (0.022 moles) of maleic anhydride, 90 ml of toluene and 10 ml of DMF. After 1 hour of stirring, 6.6 g of acetic anhydride and 0.5 g of sodium acetate is added and the mixture is stirred for a additional 1 hour. The mixture is then heated to 50° C. for 8 hours. The reaction product is then precipitated in an ice-water mixture, filtered, washed several times with water and dried overnight in a vacuum oven at 90° C. The resulting product, a bis-maleimide, is a yellow powder which turns to clear, transparent flakes upon melting. The melting point is 95° C. (DSC endotherm) and the curing temperature is 310° C. (DSC exotherm peak). It is soluble in acetone, ethylacetate, NMP, THF, MEK and BLO.

The wide difference between melting endotherm and curing exotherm gives a broad processing window for this class of polymers.

1.0 g of the bismaleimide material is then dissolved in 3.0 ml of NMP. The solution is spread on a glass plate to obtain a uniform film. The plate is dried first in an air oven at 90° C. for one hour and then at 270° C. for one hour to remove the solvent and cure the monomer. An amber color film is obtained which is slightly brittle. When placed in MEK solvent for an hour at room temperature, no change in film characteristics and no weight loss is observed.

EXAMPLE 19

A 3-neck flask purged with nitrogen and fitted with a condenser, thermometer and stirrer is charged with 4.18 g (0.005 moles) of 12F-ODA and 10 g of distilled NMP under a nitrogen atmosphere. The mixture is stirred to obtain a clear solution. 1.693 g (0.01 moles) of cis-5-nor-borene-endo-2,3-dicarboxylic acid anhydride (97% pure) (hereinafter "Nadic Anhydride") are added while stirring is continued. 13.5 g of NMP are then added and the mixture is stirred overnight at room temperature. The resulting diamic acid has an inherent viscosity of 0.12 dl/g measured at 0.5 g/dl in DMAc at 25° C.

To 20 g of the diamic acid solution, 7.07 g of acetic anhydride and 0.7 g of 3-picoline are added. The reaction mixture is stirred at room temperature for about six hours. The resulting bisnadimide is precipitated in methanol, isolated by filtration, washed with fresh methanol, and dried overnight in a vacuum oven at 85° C. It is soluble in acetone, DMAc, diglyme, MEK, NMP, THF, chloroform and BLO solvents.

1.0 g of the nadic terminated material is in 3.0 ml of NMP. The solution is spread over a glass plate to obtain a uniform film. The coated plate is dried in an air oven first at 90° C. for one hour and then at 270° C. for one hour to remove the solvent and cure the monomer. The thusly obtained film is brittle and not uniform. When placed in MEK solvent for an hour at room temperature, no weight loss is observed.

EXAMPLE 20

A 3-neck flask purged with nitrogen and fitted with a condenser, thermometer, and stirrer is charged with 8.36 g (0.01 moles) of 12F-ODA and 20 g of NMP under a nitrogen atmosphere. The mixture is stirred to obtain a clear solution. 3.81 g (0.005 moles) of 12F-DA are added while stirring is continued. 1.693 g of Nadic Anhydride is then added also under continuous stirring. After charging with 24.45 g of NMP, the reaction mixture is stirred overnight at room temperature. The resulting nadic-terminated polyamic acid has an inherent viscosity of 0.2 dl/g measured at 0.5 g/dl in DMAc at 25° C.

To 65 g of the polyamic acid solution, 16.72 g of acetic anhydride and 1.672 g of 3-picoline are added. The reaction mixture is stirred at room temperature for about six hours. The resulting nadic-terminated oligomers are precipitated in methanol, isolated by filtration, washed with fresh methanol, and dried overnight in a vacuum oven at 85° C. The final product is soluble in acetone, DMAc, diglyme, MEK, NMP, THF, chloroform and BLO solvents.

Another class of addition-type polyimide prepolymers may be characterized as having the following structure:

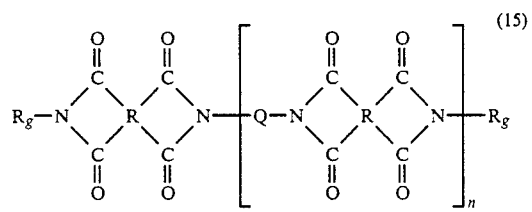
(15)

wherein n is 1 to 5, preferably n is 1 or 2, $R_g$ is

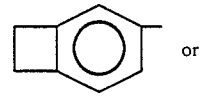 or

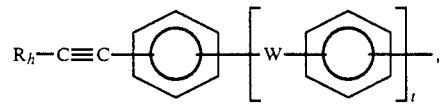, $R_h$ is H or

preferably H or $-C_6H_5$, $R_i$ is H, $-O-C_6H_5$ or $-O-C_6H_4-SO_2-C_6H_5$, preferably H, W is $-O-$, $-S-$, $-SO_2-$, $-CO-$, $-CH_2-$, $-C(CH_3)_2-$ or $-C(CF)_2-$, and t is 0 to 4, preferably t is 0.

This class of prepolymers may be prepared by first reacting the diamine of formula (4) with the tetracarboxylic acids or derivatives of formulae (6) or (7) to produce intermediate compounds having terminal anhydride, diacid, or acid-ester groups. To obtain these intermediates, excess molar amounts of the dianhydride would be used. Generally, the molar ratios of dianhydride to diamine will range from 2:1 to 4:3. The intermediates are then reacted with end-capping amines. The preferred dianhydrides are the 6F-DA dianhydride, the 12F-DA dianhydride, the BTDA dianhydride, the ODPA dianhydride, and 2,2-bis[4-(3,4-dicarboxyphenoxy)phenyl]hexafluoropropane dianhydride.

The preferred end-capping amines are 4-aminobenzocyclobutene, aminoarylacetylenes, and phenylacetylenearylamines.

The preparation of bisbenzocyclobutene substituted imide oligomers and the corresponding addition polyimides is generally shown in Tan and Arnold, "Benzocyclobutene in Polymer Synthesis I. Homopolymerization of Bisbenzocyclobutene Aromatic Imides to Form High-Temperature Resistant Thermosetting Resins," Journal of Polymer Science, vol 25, pp. 3159-3172, (1987), which is incorporated herein by reference. The benzocyclobutene substituted imide oligomers of the present invention may be characterized as having the structure:

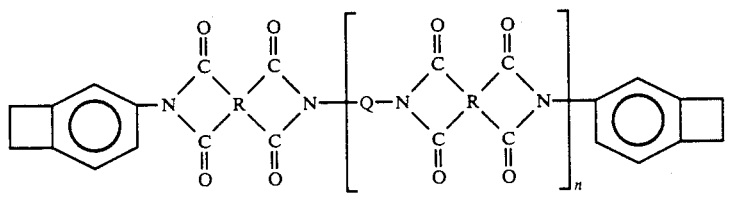

(16)

wherein n is 1 to 5, and R and Q are as defined above. Preferably, Q has the structure of formula (3) and n is 1 or 2.

The preparation of acetylene terminated imide oligomers and the corresponding addition polyimides is generally shown in U.S. Pat. No. 4,276,407 to Bilow et al. and PCT Publication No. WO 81/01293, Bilow et al., entitled "Acetylene Terminated Imide Oligomers Having Improved Solubilities and Lower Melting Points," which are incorporated herein by reference. The acetylene and phenylacetylene terminated imide oligomers of the present invention may be characterized as having the structure:

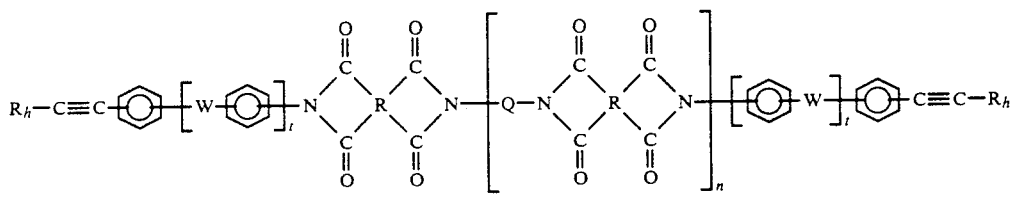

(17)

wherein n is 1 to 5, t is 0 to 4, and R, Q, $R_h$, and W are defined as above. Preferably, Q has the structure of formula (3), n is 1 or 2, and t is 0.

Suitable end capping amines having terminal acetylene or phenylacetylenyl groups are those having the structure:

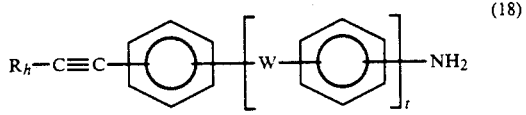

(18)

wherein t is 0 to 4, preferably t is 0, and $R_h$ and W are as defined above. The preferred acetyleneamine is 3-aminophenylacetylene and the preferred phenylacetylenylamine is 1-amino-3-phenylacetylenylbenzene.

The following examples are illustrative of imide oligomers and addition polyimides of this invention:

EXAMPLE 21

A solution of 9.4468 g (0.0113 moles) of 12F-ODA in 50 ml of NMP is added dropwise to a solution of 9.99 g (0.0225 moles) of 6F-DA in 75 ml of NMP at 50° C. in a three-necked flask equipped with stirrer under a nitrogen atmosphere. After heating the reaction contents at 50° C. for 30 minutes, a solution of 0.0225 moles of 4-aminobenzocyclobutene in 10 ml of NMP is added all at once. 75 ml of toluene is then added and the reaction mixture is refluxed (at about 143° C.) for 12 hours employing a Dean-Stark trap to remove the water. The solvent is distilled off using a mild vacuum. A residue remains which is precipitated using ethanol. A benzocyclo- butene-terminated oligomeric material product is obtained which is washed several times with ethanol and dried overnight in a vacuum oven at 90° C.

EXAMPLE 22

A solution of 9.4468 g (0.0113 moles) of 12F-ODA in 50 ml of NMP is added dropwise to a solution of 9.99 g (0.0225 moles) of 6F-DA in 75 ml of NMP at 50° C. in a three-necked flask equipped with stirrer under a nitrogen atmosphere. After heating the reaction contents at 50° C. for 30 minutes, a solution of 3.6325 g (0.0225 moles) of 3-aminophenylacetylene in 10 ml of NMP is added all at once. 75 ml of toluene is then added and the reaction mixture is refluxed (at about 143° C.) for 12 hours employing a Dean-Stark trap to remove the water. The solvent is distilled off using a mild vacuum. A brown oily residue remains which is precipitated using ethanol. A brown colored product is obtained which is washed several times with ethanol and dried overnight in a vacuum oven at 90° C.

The resulting acetylene-terminated oligomer is a brown powder having a melting point (DSC endotherm) of about 82° C. It is soluble in acetone, ethyl acetate, NMP, THF, MEK and BLO. The curing temperature is 335° C. (DSC exotherm peak) with curing range of about 250°-350° C.

The large difference between the DSC endotherm and the DSC exotherm (82°-335° C.) provides a broad processing window for this class of polymers.

The invention provides copolymers prepared by reacting the acetylene or phenylacetylene terminated oligomers of formula (17) with other known acetylene or phenylacetylene terminated monomers and oligomers. Various acetylene terminated oligomers are described in, for example, U.S. Pat. No. 4,100,138 to Bilow et al. and U.S. Pat. No. 4,276,407 to Bilow et al., which are incorporated herein by reference. U.S. Pat. No. 4,100,138 also describes the copolymerization of acetylene terminated polyimide oligomers with diethynylbenzene. Arylether compounds having terminal phenylethynyl groups are described in U.S. Pat. No. 4,513,131 to Reinhardt et al., which is incorporated herein by reference.

The invention further provides compositions of component (A) comprising known polyimides or copolyimides such as those described in U.S. Pat. Nos. 3,342,774 to Hoegger; 3,356,648 to Rogers; 3,424,718 to Angelo; 3,649,601 to Critchley et al.; 3,926,913 to Jones et al.; 3,959,350 to Rogers; 4,111,906 to Jones et al.; 4,477,648 to Jones et al.; 4,535,101 to Lee et al.; 4,595,548 to St. Clair et al.; 4,603,061 to St. Clair et al.; and 4,612,361 to Peters; which are herein incorporated by reference; or a polyimide of formula (1); or mixtures thereof; and component (B) comprising an addition-type polyimide monomer, oligomer or prepolymer of formulae (12), (13), (14), (15), (16) or (17). In another aspect, the invention provides compositions wherein component (A) is a polyimide of formula (1) and wherein component (B) is a known addition-type polyimide monomer, oligomer or prepolymer such as those described in U.S. Pat. Nos. 4,173,700 to Green et al.; 3,528,950 to Hyman, 4,233,258 to St. Clair, 4,281,102 to St. Clair et al.; 4,276,407 to Bilow et al.; 4,675,370 to Tan et al.; the Tan and Arnold publication referred to above; and PCT Publication No. WO 81/01293, Bilow et al.; all of which are incorporated herein by reference. The compositions are useful for producing films, composites and as matrix resins. When the compositions are cured, the component (B) material is polymerized forming interpenetrating networks or semi-interpenetrating networks which physically bond the molecules of the component (A) polymer in the network.

Preferably, component (A) is present in the composition in the range of from about 90 to about 10, more preferably from about 80 to about 20, percent by weight of the total combined weight of components (A) and (B). Preferably, component (B) is present in the composition in the range of from about 10 to about 90, more preferably from about 20 to about 80, percent by weight of the total combined weight of components (A) and (B).

The following examples are illustrative of the invention:

EXAMPLE 23

A composition is prepared by dissolving 1.0 g of SIXEF-44 TM polyimide (a polyimide prepared from 6F-DA dianhydride and 6F-44 diamine), available from Hoechst Celanese Corporation, Somerville, New Jersey, and 1.0 g of the bismaleimide prepared according to Example 18 in 10.0 ml of NMP. The solution is spread over a glass plate to obtain a uniform film. The coated plate is dried in an air oven first at 90° C. for one hour and then at 270° C. for one hour to evaporate the residual solvent and to cause cross-linking of the bismaleimide monomer. A uniform amber color film is obtained which is flexible. When placed in MEK solvent for an hour at room temperature, the film retains 66 percent of its original weight.

EXAMPLE 24

A composition is prepared by dissolving 1.0 g of SIXEF-44 TM polyimide (a polyimide prepared from 6F-DA dianhydride and 6F-44 diamine), available from Hoechst Celanese Corporation, Somerville, New Jersey, and 1.0 g of the bisnadimide prepared according to Example 19 in 10.0 ml of NMP. The solution is spread over a glass plate to obtain a uniform film. The coated plate is dried in an air oven first at 90° C. for one hour and then at 270° C. for one hour to evaporate the residual solvent and to cause cross-linking of the bisnadimide monomer. A uniform amber color film is obtained which is flexible. When placed in MEK solvent for an hour at room temperature, the film retains 61 percent of its original weight.

EXAMPLE 25

A composition is prepared by dissolving 1.0 g of SIXEF-44 TM polyimide (a polyimide prepared from 6F-DA dianhydride and 6F-44 diamine), available from Hoechst Celanese Corporation, Somerville, New Jersey, and 1.0 g of the acetylene-terminated oligomer prepared according to Example 22 in 10.0 ml of NMP. The solution is spread over a glass plate to obtain a uniform film. The coated plate is dried in an air oven first at 90° C. for one hour and then at 270° C. for one hour to evaporate the residual solvent and to cause cross-linking of the acetylene-terminated oligomer. A uniform film is obtained which is flexible. When placed in boiling MEK solvent for an hour, no appreciable weight loss is observed.

The present invention also provides bis(amino-imide) compounds having the structure:

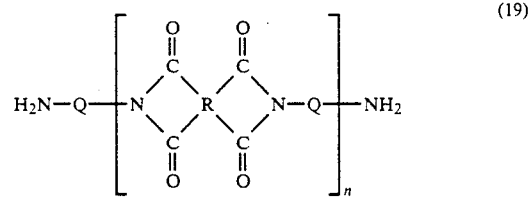

(19)

wherein
n is 1 to 5,
R is tetravalent organic radical having at least 4 carbon atoms,
Q is

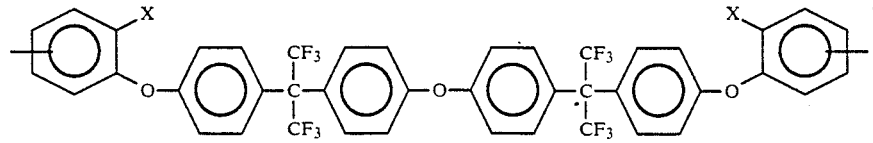

and
X is hydrogen or halogen.

Preferred are such bis(amino-imide) compounds, wherein Q has the structure:

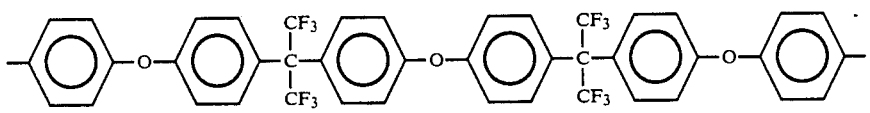

The invention also provides epoxy resin compositions. The epoxy resin composition comprises a polyfunctional epoxy resin and a curing agent. The curing agent may be a diamine of formula (4), a bis(amino-imide) compound of formula (19) or mixtures thereof.

The polyfunctional epoxy resins to which the invention relates are widely known and described in the literature and need not be redescribed herein.

The ratio by weight of epoxy resin to curing agent is preferably in the range of from about 10:90 to about 90:10, more preferably of from about 20:80 to about 80:20.

The compositions of epoxy resins and curing agent are used to impregnate fibers, such as carbon, boron and glass, and may also be filled with particulate fillers to provide high performance fiber reinforced plastic articles or filled epoxy resins which are used to fabricate a wide variety of molded articles. The preparation of epoxy resin compositions and molded articles therefrom is described in the above-referenced U.S. Pat. No. 4,244,857 to Serafini et al. and in D. A. Scola, "Synthesis and Characterization of Bisimide Amines and Bisimide Amine-Cured Epoxy Resins," Polymer Composites, Vol. 4, No. 3, pp. 154–161, (July, 1983), which is incorporated herein by reference. The compositions may also be used as adhesives.

The following examples are illustrative of the invention:

EXAMPLE 26

A solution of 10.1 g of 12F-ODA diamine in 10 g of BLO solvent is mixed with 10 g of a bisphenol A diepoxide (Interez 510) at room temperature. The mixture is cast as a film on two glass plates. One specimen is heated at 90° C. for 3 hours. The resulting film is semihard and not completely cured. The other specimen is heated at 100° C. for 3 hours. The resulting film is completely cured an yellow in color.

EXAMPLE 27

A solution of 15.2 g of 12F-ODA diamine in 10 g of BLO solvent is mixed with 10 g of a bisphenol A diepoxide (Interez 510) at room temperature. The mixture is cast as a film on two glass plates. One specimen is heated at 90° C. for 3 hours. The resulting film is semihard and not completely cured. The other specimen is heated at 110° C. for 2 hours. The resulting film is completely cured and yellow in color.

EXAMPLE 28

A solution of 16 g of the bis(amino-imide) compound of formula 19 in 10 g of BLO solvent is mixed with 10 g of a bisphenol A diepoxide (Interez 510) at room temperature. The mixture is cast on a glass plate and heated at 100° C. for 3 hours resulting in a cured film.

The solvent soluble polyimides and their polyamic acid precursors of the invention may be used in the preparation of photosensitive compositions and processed by conventional techniques to provide thermally stable relief patterns. These photosensitive compositions are useful in many applications such as photopolymerizable varnishes or protective layers such as passivation overcoat films, planarization layers in microelectronic circuits, insulating layers for multi-layered hybrid circuits and as photoresists that provide relief structures of good definition on substrates such as silicon chips, polymeric films and metal plates. They provide polymeric layers or relief structures that possess high thermal and radiation stability, excellent mechanical properties and high insulating properties. In other applications such as printing plates, the tough mechanical properties of the photopolymerizable compositions of the invention provide a means to make printing plates having the capability of giving long printing runs.

In one form, the photosensitive compositions of the invention comprise a mixture of a solvent soluble polyimide of the invention, a photoinitiator and a photopolymerizable compound containing at least two terminal ethylenically unsaturated groups.

Suitable photopolymerizable material comprises an addition polymerizable, non-gaseous (boiling temperature above 100° C. at normal atmospheric pressure), ethylenically-unsatrurated compound containing at least two terminal ethylenic groups, and being capable of forming a high molecular weight polymer by free radical initiated, chain propagating addition polymerization. Illustrative examples include tetraethylene glycol dimethacrylate, ethylene glycol dimethacrylate, trimethylol propane trimethacrylate, trimethylol propane triacrylate, polyethylene glycol (200) or (600) diacrylate, diethylene glycol dimethacrylate, pentaerythritol tetraacrylate, pentaerythritol triacrylate, 1,6-hexanediol dimethacrylate, dipentaerythritol monohydroxypentaacrylate, ethoxylated bisphenol A dimethacrylate, tripropylene glycol diacrylate, tris(2-hydroxyethyl)isocyanurate, trimethylacrylate tris(2-hydroxyethyl)triacrylate, glycerol diacrylate, glycerol triacrylate, hexamethylene diamine, diacrylamide and mixtures thereof.

Suitable photoinitiators useful in the practice of the invention are disclosed in U.S. Pat. Nos. 4,464,457; 4,465,758 and 4,619,998 which are incorporated herein by reference. A large number of substances can be used in the mixture of the present invention as polymerization intitiators which can be activated by radiation, particularly actinic light. Examples are benzoin and its derivatives, trichloromethyl-s-triazines, 1,3-bistrichloromethyl-5-(para-biphenyl)triazine-2,4,6; 1,3-bistrichloromethyl-5-(para-stilbenyl)triazine-2,4,6; acridine derivatives, for example, 9-phenylacridine, 9-p-methoxyphenylacridine, 9-acetylaminoacridine and benz(1)-acridine. Other examples are phenazine derivatives, for example, 9,10-dimethylbenz(a)phenazine and 10-methoxybenz(a)phenazine, quinoxaline derivatives, for example, 6,4',4''-trimethoxy-2,3-diphenylquinoxaline and 4',4''-dimethoxy-2,3-diphenyl-5-azaquinoxaline. The initiators are generally employed in the present invention in an amount of 0.01 to 20, preferably 0.05 to 10 percent by weight, relative to the non-volatile components of the mixture.

The mixture according to the present invention generally contains 20 to 90, preferably 30 to 80, percent by weight of solvent soluble polyimide and 80 to 10, preferably 70 to 20, percent by weight of polymerizable compounds, relative in each case to the total amount of non-volatile ethylenically unsaturated monomer and polyimide components.

The mixture can contain, as further conventional components, polymerization inhibitors, oxygen scavengers, hydrogen donors, sensitometric regulators, dyes, pigments, plasticizers and thermally activatable crosslinking agents.

It is generally advantageous to substantially isolate the compositions of the present invention from the influence of atmospheric oxygen during photopolymerization. If the composition is used in the form of a thin copying layer, it is recommended that a suitable cover film with a low permeability to oxygen be applied to the layer.

Leuco bases of triarylmethane dyes that are suitable for use in the present invention include those of Crystal Violet, Victoria Blue BH, Victoria Pure Blue BOH, Methyl Violet, and Acilan Violet S.

Suitable actinic radiation to which the composition according to the present invention is sensitive is any electromagnetic radiation whose energy is sufficient to initiate polimerization. Visible and ultrviolet light, x-rays and electron radiation are particularly suitable. Laser radiation in the visible and UV range can also be used. Short-wavelength visible and near-UV light is preferred.

The photosensitve compositions of the invention may be employed in solution which can be applied to a substrate by any conventional method, such as roller coating, dipping, spraying, whirling and spin coating. They may be prepared into and used as dry films as is taught in U.S. Pat. No. 3,469,982 to Celeste which is incorporated herein by reference.

Suitable substrates include silicon, aluminum, glass, polymeric resin boards and films, silicon dioxide, doped silicon dioxide nitride, tantalum, copper, polysilicone ceramics and aluminum/copper mixtures.

Suitable application solvents include N-methyl-pyrrolidone, dimethylformamide, γ-butyrolactone, acetone, diglyme, tetrahydrofuran, propylene glycol methyl ether, propylene glycol methyl ether acetate, and mixtures thereof. The photosensitive composition after exposure may be developed by any suitable organic solvent, e.g., γ-butyrolactone, toluene, propylene glycol methyl ether/toluene, N-methylpyrrolidone/toluene, acetone/water mixtures etc.

The following examples are illustrative of the photosensitive compositions of the invention:

EXAMPLE 29

A photosensitive composition is prepared using the solvent soluble polyimide of Example 3:

| Example 3 Polyimide | 4.0 grams |
| --- | --- |
| Pentaerythritol triacrylate | 1.5 grams |
| 1,3-bistrichloromethyl-5-(p-stilbenyl)triazine-2,4,6 | 0.1 grams |
| Dye | 0.03 grams |
| Diglyme/BLO (50/50) | 16.0 grams |

The resulting photosensitive compostion is filtered under pressure and is roller coated on an anodized aluminum plate. The coated plate is pre-baked at 90° C. for 3 minutes to obtain a resist film. The film is then overcoated with a polyvinyl alcohol protective layer (10% in water) and prebaked at 90° C. for 2 minutes. The film is then covered with a photomask having a striped pattern so that the film and the photomask are in tight contact. The film is exposed through an Addalux vacuum printer (2KW, photopolymer lamp/UV broad band radiation) for an irradiation time range of 300 sec. After the irradiation, the coating is first rinsed with hot water to remove the polyvinyl alcohol overcoat, then is developed with a mixed solution of 4 volume of BLO and 1 volume of toluene and rinsed with n-hexane to give a negative image.

Other developers include a mixture of toluene/NMP (9:1) and acetone/water (7:3).

EXAMPLE 30

A photosensitive composition is prepared and processed in accordance with the procedure of Example 29 using the solvent soluble polyimide of Example 4:

| Example 4 Polyimide | 2.0 grams |
| --- | --- |
| Pentaerythritol triacrylate | 0.4 grams |
| 1,3-bistrichloromethyl-5-(p-stilbenyl)triazine-2,4,6 | 0.3 grams |
| Diglyme/BLO (50/50) | 15.0 grams |

Similarly, the polyamic acid precursors of the polyimides of the invention may be substituted for the fully imidized polymers of the forgoing examples 30 and 31. However, after the image is developed, the film is converted to a polyimide by baking at 275°–350° C. for 0.5 to 3 hours.

The forgoing examples illustrate the use of the polymers of the invention as negative acting resists. However, they may also be used to produce positive acting compositions as illustrated by the teachings of U.S. Pat. No. 4,093,461 which are incorporated herein by reference. In these compositions, the polyamic acid precursor is mixed with a photosensitive orthoquinone or naphthoquinone diazide and processed in the conventional manner to produce a positive relief structure.

What is claimed is:

1. A composition comprising:
a fluorine-containing diamine having the formula:

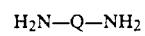

wherein
Q is

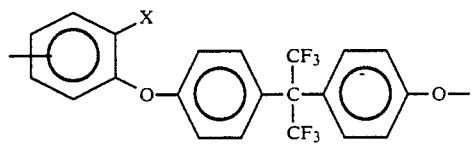

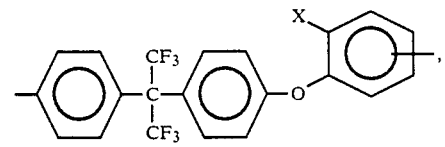

and
X is hydrogen or halogen;
a tetracarboxylic acid, or derivative thereof, having the formula,

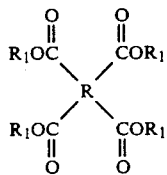

wherein
R is a tetravalent organic radical having at least 4 carbon atoms, and
$R_1$ is hydrogen or a monovalent organic radical; and
a solvent.

2. The composition of claim 1, wherein R is selected from the group consisting of

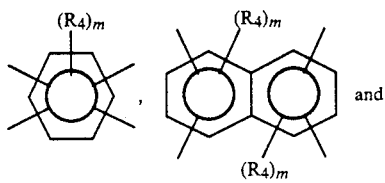 and

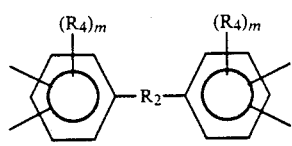

wherein $R_2$ is a carbon-carbon bond, —O—, —S—, —$SO_2$—, —CO—, —$(CH_2)_r$—,

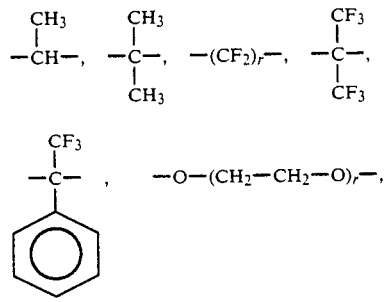

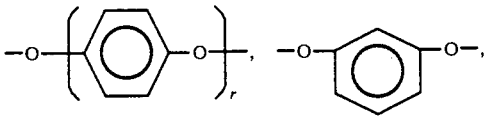

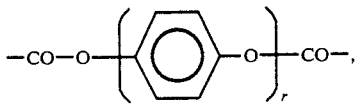

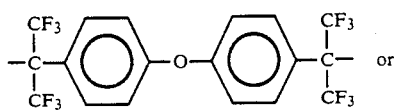

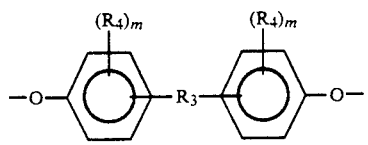

wherein $R_3$ is carbon-carbon bond —S—, —$SO_2$—, —CO—, —$CH_2$—, —$C_2H_4$—,

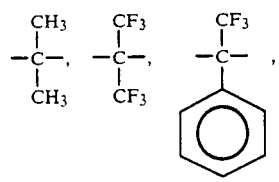

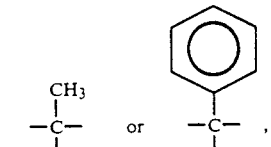

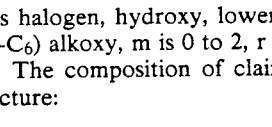

$R_4$ is halogen, hydroxy, lower ($C_1$–$C_6$) alkyl or lower ($C_1$–$C_6$) alkoxy, m is 0 to 2, r is 1 to 4, and s is 1 to 5.

3. The composition of claim 1, wherein Q has the structure:

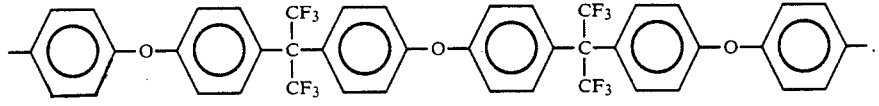

4. The composition of claim 2, wherein Q has the structure:

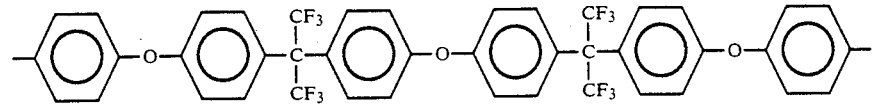

5. The composition of claim 1, wherein the solvent is propylene glycol methyl ether.

6. The composition of claim 2, wherein the solvent is propylene glycol methyl ether.

7. The composition of claim 3, wherein the solvent is propylene glycol methyl ether.

8. The composition of claim 4, wherein the solvent is propylene glycol methyl ether.

9. A polyamide polymer having groups of the structure:

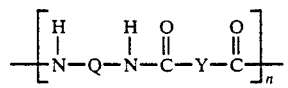

wherein
n is the number of repeating groups,
Q is

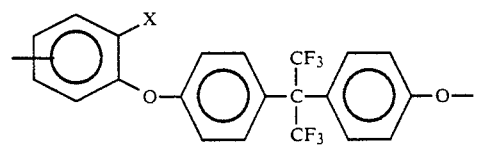

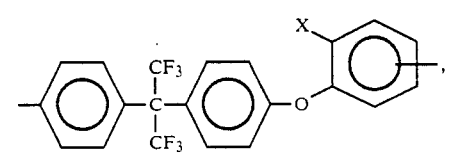

X is hydrogen or halogen, and
Y is a divalent organic radical.

10. The polyamide polymer of claim 9, wherein Y is selected from the group consisting of

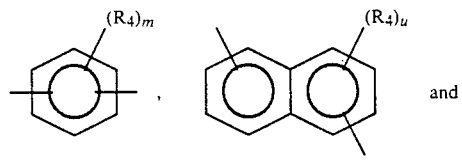 and

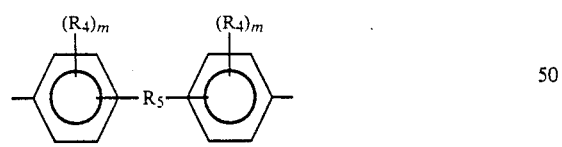

wherein $R_5$ is a carbon-carbon bond, —O—, —S—, —SO$_2$—, —CO—, —(CH$_2$)$_r$—,

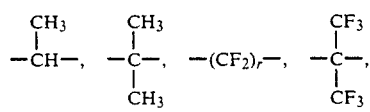

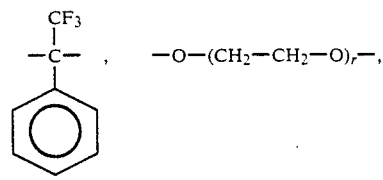

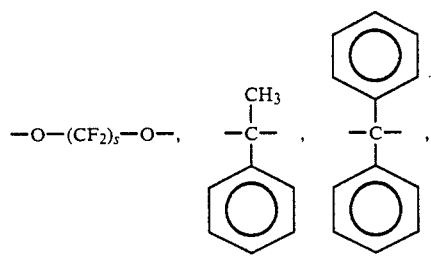

—O—(CF$_2$)$_s$—O—,

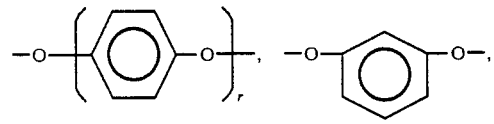

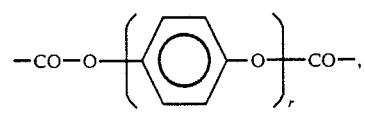

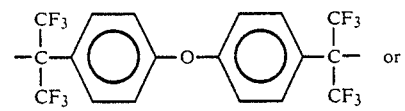

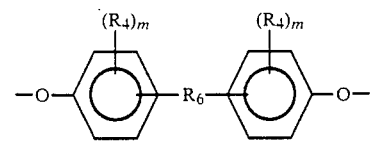

wherein $R_6$ is a carbon-carbon bond, —S—, —SO$_2$—, —CO—, —CH$_2$—, —C$_2$H$_4$—,

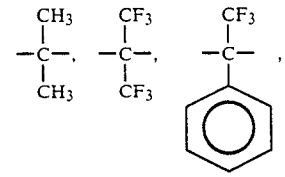

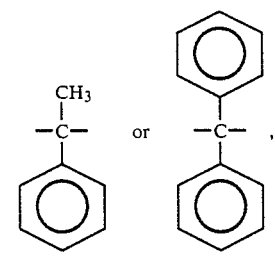

$R_4$ is hydrogen, hydroxy, lower (C$_1$-C$_6$) alkyl, or lower (C$_1$-C$_6$) alkoxy, m is 0 to 4, r is 1 to 4, m is 1 to 5, and u is 0 to 6.

11. The polyamide polymer of claim 9, wherein Q has the structure:

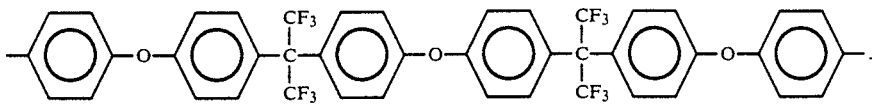

12. The polyamide polymer of claim 10, wherein Q has the structure:

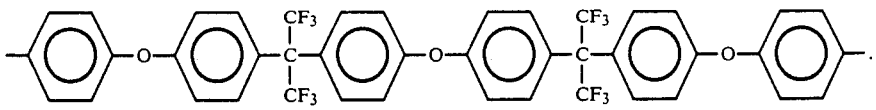

13. Polyamide polymeric material prepared by reacting:
a fluorine-containing diamine having the formula:

$$H_2N-Q-NH_2$$

wherein
Q is

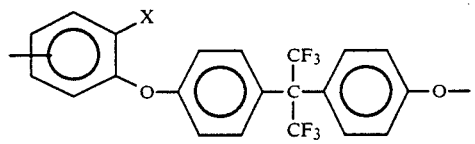

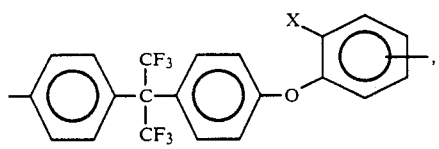

and
X is hydrogen or halogen; and
at least one dicarboxylic acid having the formula:

$$XOOC-Y-COOX$$

wherein
X is hydrogen or halogen and
Y is a divalent organic radical.

14. The polyamide polymeric material of claim 13, wherein the dicarboxylic acid is selected from the group consisting of:
phthalic acid;
isophthalic acid;
terephthalic acid;
biphenyl-3,3'-dicarboxylic acid;
biphenyl-4,4'-dicarboxylic acid;
bis(3-carboxyphenyl)methane;
bis(4-carboxyphenyl)methane;
2,2-bis-(3-carboxyphenyl)propane;
2,2-bis-(4-carboxyphenyl)propane;
naphthalene-2,6-dicarboxylic acid;
bis(3-carboxyphenyl)ether;
bis(4-carboxyphenyl)ether;
bis(3-carboxyphenyl)sulfide;
bis(4-carboxyphenyl)sulfide;
bis(3-carboxyphenyl)sulfone;
bis(4-carboxyphenyl)sulfone;
1,4-cyclohexane dicarboxylic acid;
pentanedioic acid;
hexanedioic acid;
1,4-phenylene diethanoic acid;
2,4-furandicarboxylic acid;
1,4-bis(4-carboxyphenoxy)phenylene;
1,1-bis(4-carboxyphenyl)-1-phenyl-2,2,2-trifluoroethane;
bis (4-carboxyphenyl).methyl phosphane oxide;
4,4'-dicarboxyltetraphenyl silane;
5-tertiary butyl isophthalic acid;
5-bromoisophthalic acid;
5-chloroisophthalic acid;
5-fluoroisophthalic acid;
2,2-bis(4-carboxyphenyl)hexafluoropropane;
2,2-bis[4-(4-carboxyphenoxy)phenyl]hexafluoropropane; and
1,1-bis[4-(4-carboxyphenoxy)phenyl]-1-phenyl-2,2,2-trifluoroethane.

15. The polyamide polymeric material of claim 13, wherein Q has the structure:

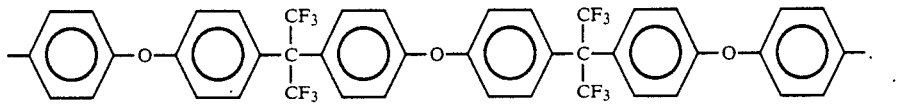

16. The polyamide polymeric material of claim 14, wherein Q has the structure:

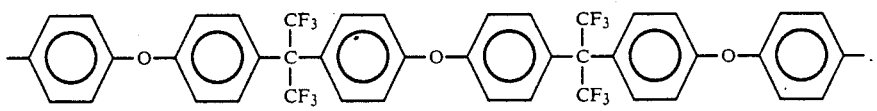

17. Copolyamide polymeric material prepared by reacting:
a fluorine-containing diamine having the formula:

$$H_2N-Q-NH_2$$

wherein

Q is

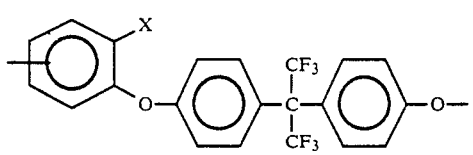

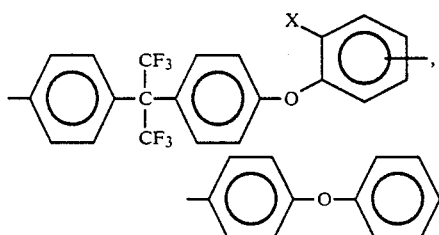

and
X is hydrogen or halogen;
at least one diamine having the formula

H₂N—A—NH₂ wherein A is a divalent organic radical; and
at least one dicarboxylic acid having the formula:

XOOC—Y—COOX wherein
X is hydrogen or halogen and
Y is a divalent organic radical.

18. The copolyamide polymeric material of claim 17, wherein Q has the structure:

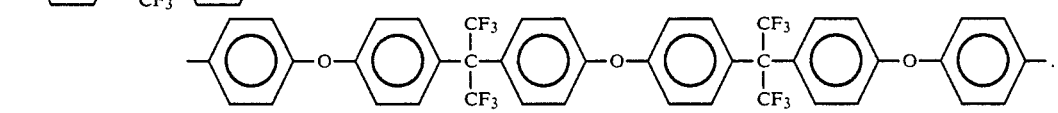

19. An aricle fabricated from a polyamide polymer of claim 9.

20. An article fabricated from a polyamide polymeric material of claim 13.

21. An article fabricated from a copolyamide polymeric material of claim 17.

* * * * *